(12) United States Patent
Araki et al.

(10) Patent No.: US 7,772,395 B2
(45) Date of Patent: Aug. 10, 2010

(54) PROCESS FOR THE PREPARATION OF PHENYL 2-PYRIMIDINYL KETONES AND THEIR NOVEL INTERMEDIATES

(75) Inventors: Koichi Araki, Ibaraki (JP); Yoshitaka Sato, Ibaraki (JP); Mark James Ford, Schmitten-Oberreifenberg (DE)

(73) Assignee: Bayer Cropscience AG, Monheim (DE)

( * ) Notice: Subject to any disclaimer, the term of this patent is extended or adjusted under 35 U.S.C. 154(b) by 744 days.

(21) Appl. No.: 11/666,496

(22) PCT Filed: Oct. 28, 2005

(86) PCT No.: PCT/EP2005/011531

§ 371 (c)(1),
(2), (4) Date: Apr. 27, 2007

(87) PCT Pub. No.: WO2006/045612

PCT Pub. Date: May 4, 2006

(65) Prior Publication Data

US 2008/0004444 A1    Jan. 3, 2008

(30) Foreign Application Priority Data

Oct. 29, 2004  (JP) .............................. 2004-317222

(51) Int. Cl.
*C07D 239/52*  (2006.01)
(52) U.S. Cl. .................................................. 544/319
(58) Field of Classification Search ................... 544/319
See application file for complete search history.

(56) References Cited

U.S. PATENT DOCUMENTS 6,458,748 B1 * 10/2002 Yoshimura et al. .......... 504/243
2004/0034251 A1    2/2004 Hiyoshi et al.

OTHER PUBLICATIONS

Bonesi, S.M. et al., "The Photooxygenation of Benzyl, Heteroarylmethyl, and Allyl Sulfides," *Eur. J. Org. Chem.* 7:1723-1728, WILEY-VCH Verlag GmbH, Weinheim (1999).

Katsutada, Y., "Difluoromethanesulfonylanilide Derivative, Its Production and Herbicide Containing the Same as Active Ingredient," *Patent Abstracts of Japan*, vol. 2000, No. 5, JPO (2000).

Mondal, E. et al., "A Useful and Environmentally Benign Synthetic Protocol for Dethiolization by Employing Vanadium Pentoxide Catalyzed Oxidation of Ammonium Bromide by Hydrogen Peroxide," *Chem. Letts.* 11:1158-1159, The Chemical Society of Japan (2001).

* cited by examiner

*Primary Examiner*—Deepak Rao
(74) *Attorney, Agent, or Firm*—Sterne, Kessler, Goldstein & Fox P.L.L.C.

(57) ABSTRACT

A process for the preparation of the compounds of the formula (I), or salts thereof, wherein R represents a hydrogen atom or difluoromethanesulfonyl, characterized in that compounds of the formula (II), or salts thereof, wherein R has the same definition as aforementioned, and n represents 0 or 1, are reacted in the presence of hydrogen peroxide and acetic acid.

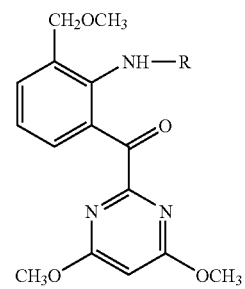

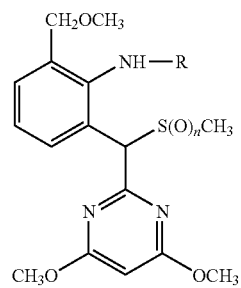

12 Claims, No Drawings

PROCESS FOR THE PREPARATION OF PHENYL 2-PYRIMIDINYL KETONES AND THEIR NOVEL INTERMEDIATES

This application is a National Stage of International Application No. PCT/EP2005/011531, filed Oct. 28, 2005, which claims the benefit of Japanese Patent Application No. 2004-317222, filed Oct. 29, 2004. The entirety of each of these applications is incorporated by reference herein.

The present invention relates to the technical field of chemical processes. Particularly, the present invention relates to a process for the preparation of phenyl 2-pyrimidinyl ketones and their novel intermediates.

Compounds of the formula (I) or salts thereof,

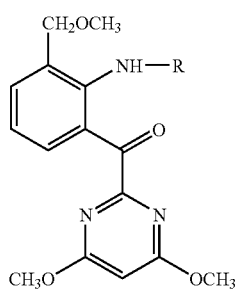

(I)

wherein
R represents a hydrogen atom or difluoromethanesulfonyl, are useful as intermediates for the preparation of industrially useful active substances, for example, compounds applicable as agricultural chemicals such as 2-[1-(4,6-dimethoxypyrimidin-2-yl)-1-hydroxymethyl]-6-methoxymethyl-N-difluoromethanesulfonanilide, a difluoromethanesulfonanilide derivative showing an action as herbicide (see for example Japanese Laid-open Patent Publication No. 2000-44546, WO 02/32882, WO 03/212861).

The known processes for preparation of the compounds of the formula (I) are not fully satisfactory, for instance, in terms of the number of reaction steps, preparation yield or safety. It has now been found that the compounds of the formula (I) or salts thereof can be obtained by a process, characterized in that a compound of the formula (II) or a salt thereof,

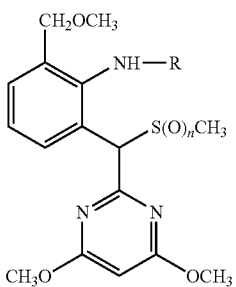

(II)

wherein R has the same definition as aforementioned in formula (I), and
n represents 0 or 1, is reacted in the presence of hydrogen peroxide and acetic acid.

According to the above-mentioned preparation process of the present invention, surprisingly, the compounds of the formula (I) can be obtained with good, high yield by using the new compounds of the formula (II), in the presence of hydrogen peroxide and acetic acid that are industrially cheaply available. The process of the present invention is, therefore, very available for the production of the compounds of the above-mentioned formula (I) on an industrial scale. The process of the present invention is described in more detail below.

The process can be illustrated by the following reaction scheme in case that, for example, 2-[1-(4,6-dimethoxypyrimidin-2-yl)-1-methylthiomethyl]-6-methoxymethyl-N-difluoro-methanesulfonanilide, hydrogen peroxide and acetic acid are used as the starting materials in the preparation process of the present invention:

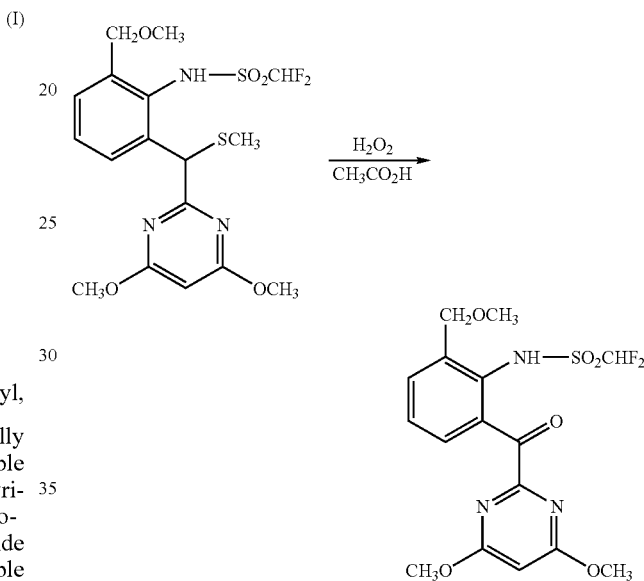

The compounds of the formula (II), or salts thereof, used as the starting materials are new compounds that are not described in the existing literature yet.

The compound of formula (II), in case that n represents 0 and R represents a hydrogen atom in the formula (II), namely, 2-[(4,6-dimethoxypyrimidinyl)-methylthiomethyl]-6-methoxymethylaniline represented by the formula (IIa),

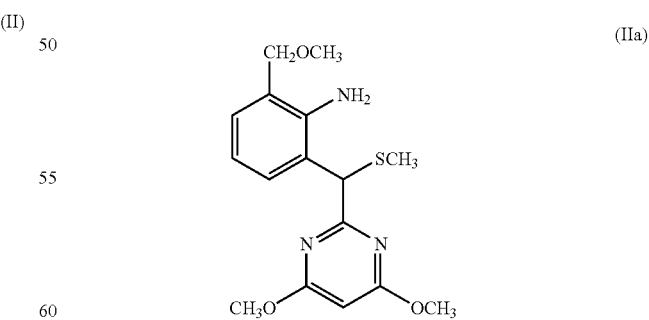

(IIa)

can be easily prepared by reacting 2-methoxymethylaniline with 2-methylthiomethyl-4,6-dimethoxypyrimidine or a salt thereof in the presence of tert-butyl hypochlorite according to the process described in WO 96/41799. The above-mentioned 2-methoxymethylaniline per se is a known compound and can be easily prepared according to the process described in Tetrahedron Letters, Vol. 30 (1), p. 47-50, 1989. The abovementioned 2-methylthiomethyl-4,6-dimethoxypyrimidine per se is also a known compound and can be easily prepared according to the process described in WO 96/41799.

The compound of formula (II) or a salt thereof, in case that n represents 0 and R represents difluoromethanesulfonyl in the aforementioned formula (II), namely, the compound represented by the following formula (IIb),

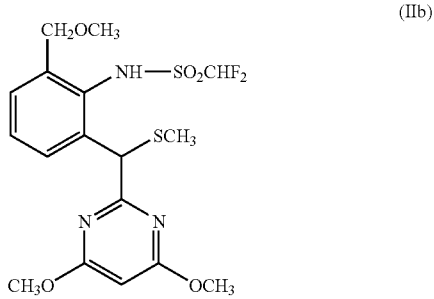

can be easily prepared by reacting the compound of the aforementioned formula (IIa) or a salt thereof with difluoromethanesulfonyl chloride according to the process described in Japanese Laid-open Patent Publication No. 2000-44546, Journal of Medicinal Chemistry, Vol. 13 (1), p. 137, 1970.

The compounds of the formula (II) or their salts, in case that n represents 1 and R represents a hydrogen atom or difluoromethanesulfonyl in the aforementioned formula (II), namely, the compounds represented by the following formula (IIc),

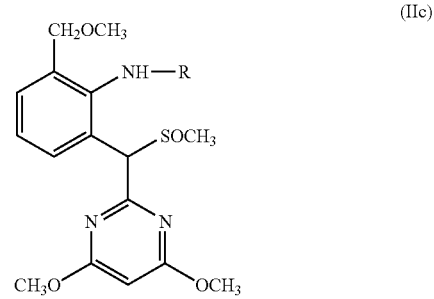

wherein R has the same definition as aforementioned, can be easily prepared by reacting the compound of the aforementioned formula (IIa) or (IIb), or salts thereof, with aqueous hydrogen peroxide analogously to the process described in Journal of Chemical Society, Perkin Trans 2, p. 405-412, 1987.

Hydrogen peroxide, used in the process, according to the present invention, is a well known compound in the field of organic chemistry and it is preferable to use, for example, aqueous hydrogen peroxide. It is preferable to use hydrogen peroxide in the range of generally about 1 to about 5 moles, particularly about 1 to about 3 moles to 1 mole of the compounds of the aforementioned formula (II). For instance it is possible to use aqueous hydrogen peroxide having a content of 30 to 35 percent by weight hydrogen peroxide in aqueous solution. It is also possible to use aqueous hydrogen peroxide having a different water content, i.e. aqueous hydrogen peroxide having from 3% to 30% by weight hydrogen peroxide in aqueous solution. It is further possible to use aqueous hydrogen peroxide with a higher content of hydrogen peroxide. In principle 100% hydrogen peroxide can be used for introducing the reagent hydrogen peroxide into the reaction. For practical purposes, preferably commercially available aqueous hydrogen peroxide having a content of 30-35% by weight of hydrogen peroxide can be used.

Acetic acid can be used in large excess and can play a role of a solvent at the same time in the process. Acetic acid can be introduced in the form of substantially anhydrous acetic acid (100% acetic acid). It is also possible to use aqueous acetic acid having various content of water. Since hydrogen peroxide can be used as aqueous hydrogen peroxide the solvent will in such a case have some content of water even if 100% acetic acid has been introduced. The possible content of water depends on the solvent property desired. So it is possible to use glacial acetic acid (96 to 99.5% aqueous acetic acid) or technical acetic acid (30-50% aqueous acetic acid) or even more diluted aqueous acetic acid.

While it is preferred to use the reagents described above without additional solvent (except some water) it is possible also to use some additional solvent if desired. Possible solvents are those which do not easily react with hydrogen peroxide. For example solvents such as halogenated aliphatic hydrocarbons such as dichloromethane or aliphatic alcohols such as ethanol can be used.

The reaction in the process, according to the present invention can be conducted at temperatures in the range of generally about 15° C. to about 120° C., preferably about 15° C. to about 100° C. Though the reaction time depends upon the reaction temperature used, it can be usually about 1 to about 96 hours, preferably about 1 to about 48 hours. And though said reaction can be conducted usually under normal pressure, it can be conducted optionally also under elevated pressure or under reduced pressure.

According to a preferred embodiment of the preparation process of the present invention, an objective compound of the formula (I) can be obtained by reacting about 1 to about 2.5 moles of aqueous hydrogen peroxide to 1 mole of a compound of the formula (II) in acetic acid at room temperature for about 1 to about 20 hours and further at about 40 to about 100° C. for about 1 to about 10 hours.

The compounds of the formula (I) and (II) can form salts by addition of a suitable inorganic or organic acid such as, for example, HCl, HBr, $H_2SO_4$ or $HNO_3$, or a mono- or bifunctional carboxylic acid or sulfonic acid, to the basic group such as, for example, amino or substituted amino, respectively, forming corresponding ammonium salts. The salts are formally ammonium salts of compounds (I) or (II) with acids, for example hydrohalic acids, such as hydrochloric acid or hydrobromic acid, furthermore phosphoric acid, nitric acid, sulfuric acid, mono- or bifunctional carboxylic acids and hydroxycarboxylic acids, such as acetic acid, oxalic acid, maleic acid, succinic acid, fumaric acid, tartaric acid, citric acid, salicylic acid, sorbic acid or lactic acid, and also sulfonic acids, such as p-toluenesulfonic acid and 1,5-naphthalenedisulfonic acid.

The acid addition compounds of the formula (I) or (II) can be obtained in a simple manner by the customary methods for forming salts, for example by dissolving a compound of the formula (I) in a suitable organic solvent, such as, for example, methanol, acetone, methylene chloride or benzene, and adding the acid at temperatures from 0 to 100° C. Salts and mixed salts of formula (I) can be formed in the course of the reaction according to the invention, especially if salts of compounds of formula (II) have been used as starting material. Salts can be can be isolated in a known manner, for example by filtration, and, if appropriate, purified by washing with an inert organic solvent.

In an preferred embodiment, the reaction is carried out by using compounds of formula (II) and isolating compounds of formula (I) in the form of their free amino compound (R=hydrogen) or the sulfamide (R=difluoromethanesulfonyl).

The work-up of the reaction mixture can be performed analogously to known methods, such as dilution with water followed by extraction with an organic solvent. Further purification methods can be followed such as chromatographic methods, distillation under reduced pressure or crystallization, optionally via a salt.

Further specific examples of the preparation of the compounds of the present invention will be shown by the following examples. The present invention, however, should not be restricted only to them in any way. In the examples ratios of solvents are volume by volume; other ratios are by weight if not otherwise specifically defined. Glacial acetic acid was used as acetic acid having 99% by weight acetic acid.

SYNTHESIS EXAMPLE 1

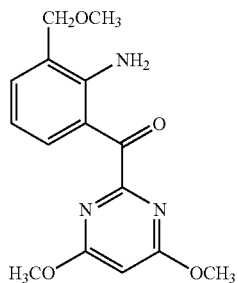

2-[(4,6-Dimethoxypyrimidin-2-yl)methylthiomethyl]-6-methoxymethylaniline (0.240 g) was diluted with glacial acetic acid (2 ml) and 30 to 35% aqueous hydrogen peroxide (0.080 ml) was added thereto at room temperature. The mixture was stirred at room temperature for 16 hours and then stirred at 40 to 50° C. for further 5 hours. The reaction solution was brought back to room temperature, diluted with water and then ethyl acetate and a small amount of sodium sulfite were added. The organic layer was separated and dried with anhydrous magnesium sulfate. After distilling off ethyl acetate under reduced pressure, the obtained crude product was purified by silica gel column chromatography using 1:5 mixed solvent of ethyl acetate and hexane as eluent to obtain 2-[(4,6-dimethoxypyrimidin-2-yl)carbonyl]-6-methoxymethylaniline (0.178 g, yield 82%);

$^1$H NMR (CDCl$_3$, 300 MHz) δ [ppm]=3.34 (3H, s), 3.96 (6H, s), 4.55 (2H, s), 6.11 (1H, s), 6.53 (1H, t), 7.13 (2H), 7.24 (1H, d), 7.37 (1H, d).

SYNTHESIS EXAMPLE 2

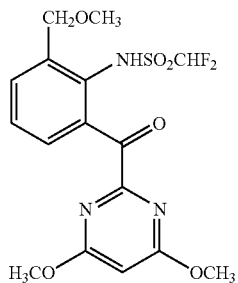

2-[1-(4,6-Dimethoxypyrimidin-2-yl)-1-methylthiomethyl]-6-methoxymethyl-N-difluoromethanesulfonanilide (0.15 g, 0.33 mmol) was diluted with glacial acetic acid (3 ml) and 30-35% aqueous hydrogen peroxide (0.032 ml) was added thereto at room temperature. The mixture was stirred at room temperature for 16 hours and then stirred at 80° C. for further 3 hours.

The reaction solution was brought back to room temperature, diluted with water and then extracted three times with ethyl acetate. The organic layer was washed with water and dried. After distilling off ethyl acetate under reduced pressure, the obtained oily substance was purified by column chromatography using 1:2 mixed solvent of ethyl acetate and hexane as eluent to obtain 2-[(4,6-dimethoxypyrimidin-2-yl)carbonyl]-6-methoxymethyl-N-difluoromethanesulfonanilide (0.1 g, yield 83%).

$^1$H NMR (CDCl$_3$, 300 MHz) δ [ppm]=3.44 (1H, s), 3.93 (6H, s), 4.74 (2H, s), 6.08-6.43 (1H, t), 6.18 (1H, s), 7.38-7.43 (1H, t, J=9 Hz), 7.62-7.65 (1H, dd, J=9 Hz, 3 Hz), 7.71-7.74 (1H, dd, J=9 Hz, 3 Hz)

SYNTHESIS EXAMPLE 3

Synthesis of a Starting Material

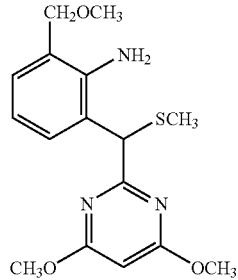

2-Methoxymethylaniline (0.68 g, 4.96 mmol) was dissolved in dichloromethane (50 ml) and the solution was cooled to −70° C. To the cooled solution a solution of tert-butyl hypochlorite (0.54 g, 4.96 mmol) in dichloromethane (1 ml) was added dropwise and the solution was stirred at −70° C. for 10 minutes. To the obtained reaction solution a solution of 2-methylthiomethyl-4,6-dimethoxypyrimidine (0.893 g, 4.46 mmol) in dichloromethane (5 ml) was added dropwise and the solution was stirred at −70° C. for 30 minutes. To the obtained reaction solution a 28% methanol solution of sodium methoxide (4 ml) was added and the solution was stirred until its temperature reached room temperature. Water was added to the reaction solution and the organic layer was separated. The water layer was further extracted twice with dichloromethane. The organic layer was washed with water and dried. Then dichloromethane was distilled off under reduced pressure and the obtained oily substance was purified by column chromatography using 1:6 mixed solvent of ethyl acetate and hexane as eluent to obtain 2-[(4,6-dimethoxypyrimidin-2-yl)-methylthiomethyl]-6-methoxymethylaniline (0.88 g, yield 53%) as oily substance;

$^1$H NMR (300 MHz, CDCl$_3$) δ [ppm]=2.03 (3H, s), 3.33 (3H, s), 3.92 (6H, s), 4.48 (3H, s), 5.08 (1H, br), 5.16 (1H, s), 5.89 (1H, s), 6.66-6.73 (1H, m), 6.99-7.02 (1H, m), 7.47-7.50 (1H, m).

SYNTHESIS EXAMPLE 4

Synthesis of a Starting Material

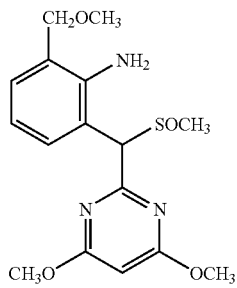

To a solution of 2-methoxymethyl-6-[1-(4,6-dimethoxypyrimidin-2-yl)-1-(methylthio)methyl]-aniline (230 mg) in glacial acetic acid (2 ml) 30 to 35% aqueous hydrogen peroxide (71 mg) was added at room temperature while stirring and the reaction solution was stirred at room temperature for 1 hour.

After diluting the reaction solution with water it was extracted three times with ethyl acetate. The organic layer was washed with water and dried. Then ethyl acetate was distilled off under reduced pressure and the obtained oily substance was purified by column chromatography using 8:1 mixed solvent of methylene chloride and acetone as eluent to obtain 2-methoxymethyl-6-[1-(4,6-dimethoxypyrimidin-2-yl)-1-(methylsulfinyl)methyl]-aniline (200 mg, yield 82%);

$^1$H NMR (CDCl$_3$, 300 MHz) δ [ppm]=2.55 (3H, s), 3.35 (3H, s), 3.95 (6H, s), 4.50 (2H), 5.1-5.3 (3H), 5.47 (1H, s), 5.96 (1H, s), 6.68 (1H, t), 7.14 (1H, d), 7.25 (1H, d).

SYNTHESIS EXAMPLE 5

Preparation of a Starting Material

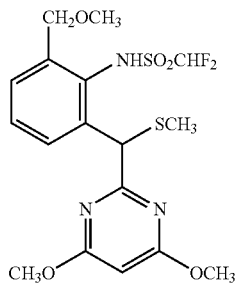

2-[(4,6-Dimethoxypyrimidin-2-yl)methylthiomethyl]-6-methoxymethylaniline (0.36 g, 1.07 mmol) was dissolved in dichloromethane (2 ml) and pyridine (0.10 g, 1.29 mmol) was added thereto. The solution was cooled to −5° C. and a solution of difluoromethanesulfonyl chloride (0.19 g, 1.29 mmol) in dichloromethane (1 ml) was added thereto. The reaction solution was stirred at room temperature for 4 days. Then water was added thereto and the mixture was extracted three times with dichloromethane.

The organic layer was washed with water and dried. Then dichloromethane was distilled off under reduced pressure and the obtained oily substance was purified by column chromatography using 1:6 mixed solvent of ethyl acetate and hexane as eluent to obtain 2-[(4,6-dimethoxypyrimidin-2-yl)-methylthiomethyl]-6-methoxymethyl-N-difluoromethanesulfonanilide (0.25 g, yield 52%) as crystals;

$^1$H NMR (300 MHz, CDCl$_3$) δ [ppm]=2.04 (3H, s), 3.40 (3H, s), 3.94 (6H, s), 4.58 (1H, d, J=12 Hz), 4.71 (1H, d, J=12 Hz), 5.70 (1H, s), 5.89 (1H, s), 6.70 (1H, t), 7.35-7.46 (2H, m), 8.02-8.05 (1H, m).

SYNTHESIS EXAMPLE 6

Preparation of a Starting Material

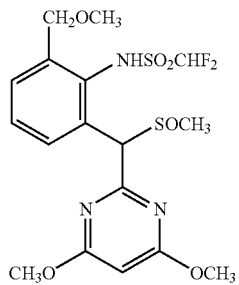

To a solution of 2-[1-(4,6-dimethoxypyrimidin-2-yl)-1-methylthio]-6-methoxymethyl-N-difluoromethanesulfonanilide (0.50 g, 1.11 mmol) in glacial acetic acid (8 ml), 30 to 35% aqueous hydrogen peroxide (0.14 g, 1.34 mmol)) was added at room temperature while stirring. The reaction solution was stirred at room temperature for 1.5 hours. The reaction solution was diluted with water and then extracted three times with ethyl acetate. The organic layer was washed with water and dried. After distilling off ethyl acetate under reduced pressure, the obtained oily substance was purified by column chromatography using 2:1 mixed solvent of ethyl acetate and hexane as eluent to obtain 2-[(4,6-dimethoxypyrimidin-2-yl)-1-methylsulfinylmethyl]-6-methoxymethyl-N-difluoromethanesulfonanilide (0.51 g, yield 98%);

$^1$H NMR (CDCl$_3$, 300 MHz), 2.44 (1.2H, s), 2.74 (1.8H, s), 3.40 (3H, s), 3.91 (2.4H, s), 3.93 (3.6H, s), 4.62-4.76 (2H, m), 5.93 (0.6H, s), 6.02 (0.6H, s), 6.03 (0.4H, s), 6.33 (0.4H, s), 6.60 (0.6H, t), 6.71 (0.4H, t), 7.33-7.60 (3H, m);

the above-mentioned compound obtained was estimated from NMR as about 3:2 mixture of diastereomers.

The invention claimed is:

1. A process for the preparation of a compound of formula (I) or a salt thereof,

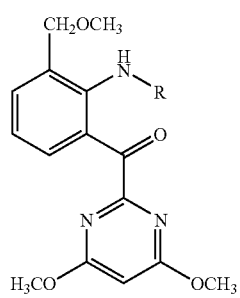

wherein
R is a hydrogen atom or difluoromethanesulfonyl, comprising:
reacting hydrogen peroxide and acetic acid with a compound of formula (II) or a salt thereof,

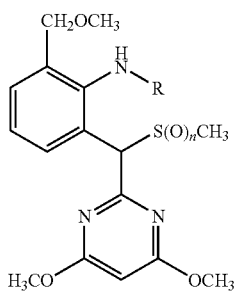

(II)

wherein

R is defined as in the compound of formula (I), and n is 0 or 1.

2. A process according to claim 1, wherein R is a hydrogen atom.

3. A process according to claim 1, wherein R is difluoromethanesulfonyl.

4. A process according to claim 1, wherein said hydrogen peroxide is aqueous.

5. A process according to claim 1, wherein said acetic acid is 96 to 99.5% aqueous acetic acid.

6. A process according to claim 1, wherein a compound of formula (II) is reacted with hydrogen peroxide in a ratio of 1 mole of compound (II) to 1 to 5 moles of hydrogen peroxide.

7. A process according to claim 1, wherein the reaction is conducted at temperatures in the range of 15° C. to 1200° C.

8. A compound of formula (II) or a salt thereof,

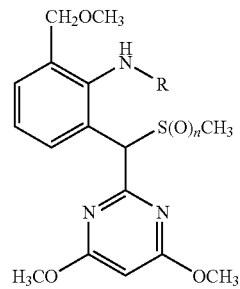

(II)

wherein

R is a hydrogen atom or difluoromethanesulfonyl, and n is 0 or 1.

9. A compound in according to claim 8, wherein R is a hydrogen atom and n is 0.

10. A compound according to claim 8, wherein R is a hydrogen atom and n is 1.

11. A compound in according to claim 8, wherein R is difluoromethanesulfonyl and n is 0.

12. A compound according to claim 8, wherein R is difluoromethanesulfonyl and n is 1.

* * * * *